United States Patent [19]

Miller et al.

[11] Patent Number: 6,083,505
[45] Date of Patent: Jul. 4, 2000

[54] 1H-IMIDAZO[4,5-C]QUINOLIN-4-AMINES AS VACCINE ADJUVANTS

[75] Inventors: Richard L. Miller, White Bear Lake; Mark A. Tomai, Oakdale, both of Minn.; David I. Bernstein, Loveland, Ohio; Christopher J. Harrison, Omaha, Nebr.

[73] Assignee: 3M Innovative Properties Company, St. Paul, Minn.

[21] Appl. No.: 08/217,774

[22] Filed: Mar. 24, 1994

Related U.S. Application Data

[63] Continuation of application No. 07/869,386, Apr. 16, 1992, abandoned.

[51] Int. Cl.[7] .................. A61K 39/385; A61K 45/00
[52] U.S. Cl. .................... 424/193.1; 424/278.1; 424/204.1; 424/231.1; 424/236.1; 424/93.1; 424/196.11; 546/26; 546/79; 546/81; 546/84; 548/100; 548/125; 548/126
[58] Field of Search .................. 424/192.1, 204.1, 424/231.1, 234.1, 236.1, 265.1, 274.1, 277.1, 278.1, 93.1, 93.4, 93.6, 193.1, 196.11; 546/26, 79, 81, 84; 548/100, 125, 126

[56] References Cited

U.S. PATENT DOCUMENTS

| | | | |
|---|---|---|---|
| 4,619,827 | 10/1986 | Bull et al. | 424/89 |
| 4,689,224 | 8/1987 | Bull et al. | 424/89 |
| 4,689,338 | 8/1987 | Gerster | 514/293 |
| 4,716,168 | 12/1987 | Alaimo et al. | 514/293 |
| 4,806,352 | 2/1989 | Cantrell | 424/92 |
| 4,929,624 | 5/1990 | Gerster et al. | 514/293 |
| 5,015,476 | 5/1991 | Cochrum et al. | 424/423 |
| 5,026,543 | 6/1991 | Rijke | 424/88 |
| 5,026,546 | 6/1991 | Hilgers et al. | 424/88 |
| 5,037,986 | 8/1991 | Gerster | 546/82 |
| 5,149,529 | 9/1992 | Ho et al. | 424/88 |
| 5,268,376 | 12/1993 | Gerster | 514/293 |
| 5,346,905 | 9/1994 | Gerster | 514/293 |
| 5,389,640 | 2/1995 | Gerster et al. | 514/293 |

FOREIGN PATENT DOCUMENTS

| | | |
|---|---|---|
| 0376534 | 7/1990 | European Pat. Off. . |
| 385630 | 9/1990 | European Pat. Off. ...... C07D 471/04 |
| 0394026 | 10/1990 | European Pat. Off. . |
| 98/18810 | 5/1998 | WIPO . |

OTHER PUBLICATIONS

Warren et al "Current Status of Immunological Adjuvants", *Ann. Rev. Immunol.*, 1986, 4, pp. 369–388.
*J. Immunol.*, 1975, 115, 575–578 (Smith et al.).
*Infection and Immunity*, 1978, 22, 62–68 (Langford et al.).
*J. Infectious Diseases*, 1986, 153, (Poindexter et al.) 772–778.
*Immunology*, 1986, 58, 203 (Micusan et al.).
*J. Clin. Invest.*, 1984, 73, 1312 (Ikejima et al.).
Chen, M., Griffith, B.P., Lucia, H.L. and Hsiung, G.D., "Efficacy of S–26308 Against Guinea Pig Cytomegalovirus Infection", *Antimicrobial Agents and Chemotherapy*, 32, (5), 678–683, 1988.
Harrison, C.J., Jenski, L., Voychehovski, T., and Bernstein, D.I., "Modification of Immunological Responses and Clinical Disease During Topical R–837 Treatment of Genital HSV–2 Infection", *Antiviral Research* (10), 209–224, 1988.
Kende, M., Lupton, H.W., and Canonico, P.G., "Treatment of Experimental Viral Infections with Immunomodulators", *Advances in the Biosciences* (68), 51–63, 1988.
S–26308. Drugs of the Future 14, (9), 870–871, 1989.
Bernstein, D.I., Harrison, C.J., "Effects of the Immunomodulating Agent R–837 on Acute and Latent Herpes Simplex Virus Type 2 Infections", *Antimicrobial Agents and Chemotherapy* 33, (9), 1511–1515, 1989.
S–26308. Drug of the Future (15), No. 9, 967–968, 1990.
Harrison, C.J., Stanberry, L.R., and Bernstein, D.I., "Effects of Cytokines and R–837, a Cytokine Inducer, on UV–Irradiation Augmented Recurrent Genital Herpes in Guinea Pigs", *Antiviral Research* (15), 315–322, 1991.
Edelman et al (1990) "Adjuvants" Intern. Rev. Immunol. 7:51–66.
Allison et al (1992) "Immunological Adjuvants and Their Mode of Action" in *Vaccines: New Approaches to Immunological Problems* ed by R. W. Ellis, Butterworth–Heinemann, MA pp. 431–449.
*Mechanisms of Interferon Actions* vol. II ed. L. M. Pfeffer CRC Press, Inc Boca Raton, Fl Chapter 12 "Interferon–Mediated Modulation of the Immune System" by H.M. Johnson pp. 59–77.
Playfair et al (1987) Clin. Exp. Immunol 67:5–10.
Grob et al (1984) Eur J. Clin. Microbiol 3(3):195–198.
Heath et al (1989) Immunology 67:520–524.

*Primary Examiner*—Keith D. MacMillan
*Assistant Examiner*—P. Ponnaluri
*Attorney, Agent, or Firm*—Ted K. Ringsred; MarySusan Howard; Robert W. Sprague

[57] ABSTRACT

An immunogen/vaccine adjuvant composition containing an immunogen in an amount effective to stimulate an immune response and as a vaccine adjuvant a 1H-imidazo[4,5-c] quinolin-4-amine in an amount effective to increase the immune response to the immunogen.

16 Claims, No Drawings

1H-IMIDAZO[4,5-C]QUINOLIN-4-AMINES AS VACCINE ADJUVANTS

This is a continuation of application Ser. No. 07/869,386 filed Apr. 16, 1992, which is now abandoned.

FIELD OF THE INVENTION

This invention relates to compositions comprising a vaccine and a vaccine adjuvant. In another aspect this invention relates to vaccine adjuvants.

DESCRIPTION OF THE RELATED ART

In the field of immunology it has been well known for many years that immune response to certain antigens which are otherwise weakly immunogenic can be enhanced through the use of vaccine adjuvants. Such adjuvants potentiate the immune response to specific antigens and are therefore the subject of considerable interest and study within the medical community.

A wealth of knowledge concerning the complexity and sophistication of immune regulation ("immunomodulation") has become available in the past decade. Coupled with currently available biosynthetic and recombinant DNA technology, this knowledge is permitting development of vaccines possessing antigenic epitopes that were previously impossible to produce. For example, currently available vaccine candidates include synthetic peptides mimicking streptococcal, gonococcal, and malarial antigens. These purified antigens are generally weak immunogens, however, that require adjuvants in order to evoke protective immunity. Unfortunately, however, as detailed below, conventional vaccine adjuvants possess a number of drawbacks which limit their overall use and effectiveness.

Over the years, Freund's complete or incomplete (i.e., without mycobacteria) adjuvants have been considered the classic adjuvants to which most other adjuvants are compared. However, clinical use of such adjuvants in animals or humans is precluded because they produce granulomas at the site of injection; fever and other toxic effects; and tuberculin hypersensitivity. Other materials, such as mineral oil and aluminum hydroxide, have also been used as adjuvants, but they invariably suffer from disadvantages. For example, mineral oil is known to produce tissue irritation and to be potentially oncogenic. Aluminum hydroxide, the only approved adjuvant in the United States, also induces granulomas at the inoculation site and furthermore it does not effectively induce cell mediated immunity. Moveover, many of the adjuvants currently available have limited utility because they contain components which are not metabolizable in humans. Additionally, most adjuvants are difficult to prepare in that they may require time consuming procedures and the use, in some cases, of elaborate and expensive equipment to formulate a vaccine and adjuvant system.

For a thorough discussion of various immunological adjuvants, see "Current Status of Immunological Adjuvants", Ann. Rev. Immunol., 1986, 4, pp. 369–388. See also U.S. Pat. Nos. 4,806,352; 5,026,543; and 5,026,546 for disclosures of various vaccine adjuvants appearing in the patent literature.

In recent years, in an ongoing attempt to find new adjuvants for vaccines which would overcome the drawbacks and deficiencies of conventional adjuvants, there have been those within the medical community who have postulated that the adjuvant potential of various substances can be directly correlated to their immunomodulatory capabilities, i.e., the ability to affect the immune system in some fashion. For example, increased cytokine (e.g., TNF, IL-2, IL-6, IL-8, alpha-interferon, etc.) production by a particular substance could be interpreted as being indicative of a beneficial effect if used as an adjuvant for vaccines. The latter, however, has not always been found to be true.

Staphylococcus enterotoxin B, for example, has not been found to be immunoenhancing for either cell-mediated (e.g., cytotoxic T-cell lymphocytes) or humoral immune responses (i.e., specific antibody production) even though the enterotoxin has been shown to increase the level of production of various cytokines such as IL-2, TNF, gamma-interferon, etc. (see, e.g., J. Immunol., 1975, 115, 575 (Smith et al.) and Infection and Immunity, 1978, 22, 62 (Lansford et al.)) The same situation has been shown to be true for Toxic Shock Syndrome toxin-1 and a variety of other substances as well (see, e.g., J. Infectious Diseases, 1986, 153, 722 (Poindexter et al.), Immunology, 1986, 58, 203 (Meusen et al.), and J. Clin. Invest., 1984, 73, 1312 (Ikejima et al.)).

In view of the foregoing, it can be readily seen that the general immunomodulatory effects of various substances is not necessarily an accurate barometer of their immunoenhancing capabilities. Accordingly, this fact has frustrated the search for materials which would be effective adjuvants for various vaccines and as a result such materials are constantly sought by and are in high demand within the medical community. Clearly, an adjuvant formulation which elicits potent cell-mediated and humoral immune responses to a wide range of antigens in humans and domestic animals, but lacking the side effects of conventional adjuvants, such as Freund's complete adjuvant, would be highly desirable. It was against this background that Applicants began their search for an effective vaccine adjuvant.

SUMMARY OF THE INVENTION

This invention provides an immunogen/vaccine adjuvant composition comprising an immunogen in an amount effective to stimulate an immune response and as a vaccine adjuvant a 1H-imidazo[4,5-c]quinolin-4-amine in an amount effective to increase the immune response to the immunogen.

This invention also provides a method of increasing the immune response to an immunogen, comprising the step of administering (i) the immunogen in an amount effective to stimulate an immune response, and (ii) as a vaccine adjuvant a 1H-imidazo[4,5-c]quinolin-4-amine in an amount effective to increase the immune response.

Certain 1H-imidazo[4,5-c]quinolin-4-amines have been disclosed as antiviral agents (see, e.g., U.S. Pat. Nos. 4,689, 338 (Gerster) and 4,929,624 (Gerster et al.), European Patent Application 90.301776.3 (Gerster) and commonly assigned copending applications 07/838,475 (Gerster et al.), 07/754,610 (Gerster et al.), and 07/788,565 (Gerster et al.) all incorporated herein by reference). Certain of these compounds are also known to induce biosynthesis of cytokines such as interferons, interleukins, and tumor necrosis factor in humans and in mice. In this invention, however, the 1H-imidazo[4,5-c]quinolin-4-amine functions as a vaccine adjuvant (i.e., it is an immunostimulatory substance that potentiates humoral and/or cell mediated immune responses to an immunogen). These compounds are relatively small synthetic organic molecules that are well characterized and substantially free of contaminants that can cause undesired effects. They are generally suitably nontoxic and do not cause undue irritation at the site of injection. Therefore this invention avoids the shortcomings seen with some vaccine adjuvants of the prior art.

DETAILED DESCRIPTION OF THE INVENTION

As used herein the term "immunogen/vaccine adjuvant composition" refers to a combination of an immunogen and a 1H-imidazo[4,5-c]quinolin-4-amine, whether that combination is in the form of an admixture of the two components in a pharmaceutically acceptable carrier or in the form of separate, individual components, for example in the form of a kit comprising an immunogen as one component and the 1H-imidazo[4,5-c]quinolin-4-amine as another component.

The vaccine adjuvant component of a composition of the invention is a 1H-imidazo[4,5-c]quinolin-4-amine. It has been found that compounds of this class induce biosynthesis of a variety of cytokines in human and murine cells. While the particular profile of cytokine induction varies to some extent from compound to compound within this class, it is thought that the general profile of cytokine induction common to the compounds of the class is responsible for the vaccine adjuvant activity of the compounds. Also, some compounds of this class have been shown to be potent stimulants of β-lymphocytes and therefore capable of increasing humoral immune response.

Preferably the 1H-imidazo[4,5-c]quinolin-4-amine is a compound defined by one of Formulas I–V below:

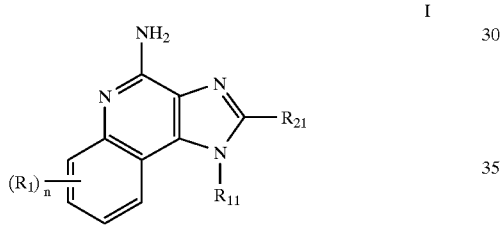

wherein $R_{11}$ is selected from the group consisting of alkyl, hydroxyalkyl, acyloxyalkyl, benzyl, (phenyl)ethyl and phenyl, said benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that if said benzene ring is substituted by two of said moieties, then said moieties together contain no more than 6 carbon atoms; $R_{21}$ is selected from the group consisting of hydrogen, alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that when the benzene ring is substituted by two of said moieties, then the moieties together contain no more than 6 carbon atoms; and each $R_1$ is independently selected from the group consisting of alkoxy of one to about four carbon atoms, halogen and alkyl of one to about four carbon atoms, and n is an integer from 0 to 2, with the proviso that if n is 2, then said $R_1$ groups together contain no more than 6 carbon atoms;

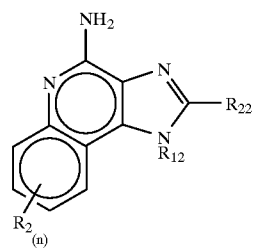

wherein $R_{12}$ is selected from the group consisting of straight chain or branched chain alkenyl containing 2 to about 10 carbon atoms and substituted straight chain or branched chain alkenyl containing 2 to about 10 carbon atoms, wherein the substituent is selected from the group consisting of straight chain or branched chain alkyl containing 1 to about 4 carbon atoms and cycloalkyl containing 3 to about 6 carbon atoms; and cycloalkyl containing 3 to about 6 carbon atoms substituted by straight chain or branched chain alkyl containing 1 to about 4 carbon atoms; and $R_{22}$ is selected from the group consisting of hydrogen, straight chain or branched chain alkyl containing one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to about four carbon atoms, straight chain or branched chain alkoxy containing one to about four carbon atoms, and halogen, with the proviso that when the benzene ring is substituted by two such moieties, then the moieties together contain no more than 6 carbon atoms; and each $R_2$ is independently selected from the group consisting of straight chain or branched chain alkoxy containing one to about four carbon atoms, halogen, and straight chain or branched chain alkyl containing one to about four carbon atoms, and n is an integer from zero to 2, with the proviso that if n is 2, then said $R_2$ groups together contain no more than 6 carbon atoms;

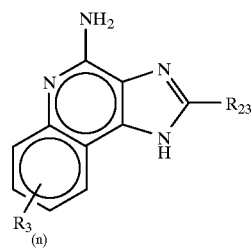

wherein $R_{23}$ is selected from the group consisting of hydrogen, straight chain or branched chain alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl of one to about four carbon atoms, straight chain or branched chain alkoxy of one to about four carbon atoms, and halogen, with the proviso that when the benzene ring is substituted by two such moieties, then the moieties together contain no more than 6 carbon atoms; and each R₃ is independently selected from the group consisting of straight chain or branched chain alkoxy of one to about four carbon atoms, halogen, and straight chain or branched chain alkyl of one to about four carbon atoms, and n is an integer from zero to 2, with the proviso that if n is 2, then said R₃ groups together contain no more than 6 carbon atoms;

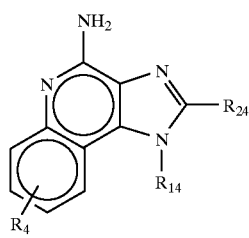

IV

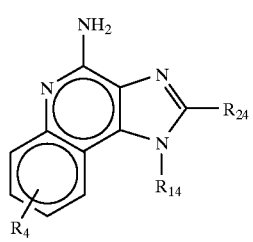

IV wherein

R₁₄ is —CHR_AR_B wherein

R_B is hydrogen or a carbon-carbon bond, with the proviso that when R_B is hydrogen R_A is alkoxy of one to about four carbon atoms, hydroxyalkoxy of one to about four carbon atoms, 1-alkynyl of two to about ten carbon atoms, tetrahydropyranyl, alkoxyalkyl wherein the alkoxy moiety contains one to about four carbon atoms and the alkyl moiety contains one to about four carbon atoms, 2-, 3-, or 4-pyridyl, and with the further proviso that when R_B is a carbon-carbon bond R_B and R_A together form a tetrahydrofuranyl group optionally substituted with one or more substituents independently selected from the group consisting of hydroxy and hydroxyalkyl of one to about four carbon atoms;

R₂₄ is selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and R₄ is selected from the group consisting of hydrogen, straight chain or branched chain alkoxy containing one to about four carbon atoms, halogen, and straight chain or branched chain alkyl containing one to about four carbon atoms;

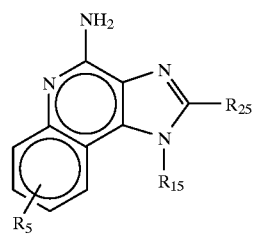

V

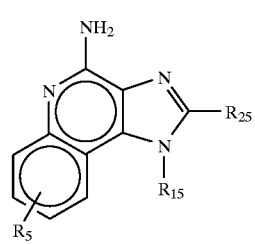

V wherein

R₁₅ is selected from the group consisting of: hydrogen; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and he alkyl moiety contains one to about six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;

R₂₅ is

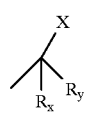

wherein

R_x and R_y are independently selected from the group consisting of hydrogen, alkyl of one to about four carbon atoms, phenyl, and substituted phenyl wherein the substituent is elected from the group consisting of alkyl of one to about four carbon atoms, alkoxy of one to about four carbon atoms, and halogen;

X is selected from the group consisting of alkoxy containing one to about four carbon atoms, alkoxyalkyl wherein the alkoxy moiety contains one to about four carbon atoms and the alkyl moiety contains one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, alkylthio of one to about four carbon atoms; and $R_5$ is selected from the group consisting of hydrogen, straight chain or branched chain alkoxy containing one to about four carbon atoms, halogen, and straight chain or branched chain alkyl containing one to about four carbon atoms;

or a pharmaceutically acceptable salt of any of the foregoing.

The compounds recited above are disclosed and claimed in the several patents and applications noted above in the Summary of the Invention.

In instances where n can be zero, one, or two, n is preferably zero or one.

The substituents $R_1$–$R_5$ above are generally designated "benzo substituents" herein. The preferred benzo substituent is hydrogen.

The substituents $R_{11}$–$R_{15}$ above are generally designated "1-substituents" herein. The preferred 1-substituent is 2-methylpropyl or 2-hydroxy-2-methylpropyl.

The substituents $R_{21}$–$R_{25}$ above are generally designated "2-substituents" herein. The preferred 2-substituents are hydrogen, alkyl of one to about six carbon atoms, alkoxyalkyl wherein the alkoxy moiety contains one to about four carbon atoms and the alkyl moiety contains one to about four carbon atoms. Most preferably the 2-substituent is hydrogen, methyl, or ethoxymethyl.

Preferred compounds 1H-imidazo[4,5-c] quinolin-4-amines include:

1-(2-methylpropyl)-1H-imidazo[4,5-c]quinolin-4-amine;

1-(2-hydroxy-2-methylpropyl)-1H-imidazo[4,5-c]quinolin-4-amine; and 1-(2-hydroxy-2-methylpropyl)-2-methyl-1H-imidazo[4,5-c]quinolin-4-amine; and 1-(2-hydroxy-2-methylpropyl)-2-ethoxymethyl-1H-imidazo[4,5-c]quinolin-4-amine.

The 1H-imidazo[4,5-c]quinolin-4-amine is present (or administered, as appropriate to the form of the immunogen/vaccine adjuvant composition) in an amount effective to increase the immune response to a particular immunogen. For example, in instances where the compound is administered independent of the immunogen, e.g., by separate injection, the compound is generally administered in an amount of about 0.003 to about 5 mg/kg. The particular amount that constitutes an effective amount, however, depends to some extent upon certain factors, including the particular 1H-imidazo[4,5-c]quinolin-4-amine, the particular immunogen being administered and the amount thereof, the immune response that is to be enhanced (humoral or cell mediated), the state of the immune system (e.g., suppressed, compromised, stimulated), the method and order of administration of the compound and the immunogen, the species, and the desired therapeutic result. Accordingly it is not practical to set forth generally the amount that constitutes an effective amount of the 1H-imidazo[4,5-c]quinolin-4-amine. Those of ordinary skill in the art, however, can readily determine the appropriate amount with due consideration of such factors.

As shown in the Examples that follow, a 1H-imidazo[4,5-c]quinolin-4-amine has the effect of enhancing both humoral and cell mediated immune response. Therefore the immunogen can be any material that raises either humoral or cell mediated immune response, or both. Suitable immunogens include live viral and bacterial immunogens and inactivated viral, tumor-derived, protozoal, organism-derived, fungal, and bacterial immunogens, toxoids, toxins, polysaccharides, proteins, glycoproteins, peptides, and the like. Conventional vaccine preparations, such as those used in connection with BCG (live bacteria), cholera, plague, and typhoid (killed bacteria), hepatitis B, influenza, inactivated polio, and rabies (inactivated virus), measles, mumps, rubella, oral polio, and yellow fever (live virus), tetanus and diphtheria (toxoids), hemophilus influenzae b, meningococcal, and pneumococcal (bacterial polysaccharides) can be used as the immunogen. Because the 1H-imidazo[4,5-c]quinolin-4-amine compounds induce biosynthesis of antiviral cytokines, in the instance of a live viral immunogen it is preferred to administer the virus prior to administration of the adjuvant compound in order that the viral infection can be established.

Furthermore, it is contemplated that certain currently experimental immunogens, especially materials such as recombinant proteins, glycoproteins, and peptides that do not raise a strong immune response, will also find use in connection with a 1H-imidazo[4,5-c]quinolin-4-amine. Exemplary experimental subunit immunogens include those related to viral disease such as adenovirus;, AIDS, chicken pox, cytomegalovirus, dengue, feline leukemia, fowl plague, hepatitis A, hepatitis B, HSV-1, HSV-2, hog cholera, influenza A, influenza B, Japanese encephalitis, measles, parainfluenza, rabies, respiratory syncytial virus, rotavirus, wart, and yellow fever.

Preferred immunogens for use in this invention include T-dependent immunogens such as viral pathogens and tumor-derived immunogens.

A particular preferred immunogen for use in this invention is a herpes simplex II (HSV-2) glycoprotein subunit preparation prepared as described in *J. Infect. Dis.* 1987, 155, 914 (Stanberry et al.).

In the method of the invention, the immunogen is administered in an amount effective to stimulate an immune response. The amount that constitutes an effective amount depends to some extent upon certain factors, including the particular immunogen, the particular adjuvant being administered and the amount thereof, the immune response that is to be enhanced (humoral or cell mediated), the state of the immune system (e.g., suppressed, compromised, stimulated), the method and order of administration of the compound and the immunogen, and the desired therapeutic result. Accordingly it is not practical to set forth generally the amount that constitutes an effective amount of immunogen. Those of ordinary skill in the art, however, can readily determine the appropriate amount with due consideration of such factors.

The immunogen/vaccine adjuvant compositions of the invention can contain further pharmaceutically acceptable ingredients, excipients, carriers, and the like well known to those skilled in the art.

The immunogen/vaccine adjuvant composition of the invention can be administered to animals, e.g., mammals (human and non-human), fowl, and the like according to conventional methods well known to those skilled in the art (e.g., orally, subcutaneously, nasally, topically). It is preferred to administer the 1H-imidazo[4,,5-c]quinolin-4-amine simultaneously with the immunogen (together in admixture or separately, e.g., orally or by separate injection) or subsequent to challenge with the immunogen. As seen in the Examples that follow (and as is common in the art) administration of the vaccine adjuvant prior to challenge with the immunogen can result in immunosuppression rather than stimulation.

The following Examples are provided to illustrate the invention.

In the Examples, "Compound A" designates 1-(2-methylpropyl)-1H-imidazo[4,5-c]quinolin-4-amine. "Compound B" designates 1-(2-hydroxy-2-methylpropyl)-1H-imidazo[4,5-c]quinolin-4-amine. "Compound C" designates 1-(2-hydroxy-2-methylpropyl)-2-methyl-1H-imidazo[4,5-c]quinolin-4-amine. "Compound D" designates 1-(2-hydroxy-2-methylpropyl)-2-ethoxymethyl-1H-imidazo[4,5-c]quinolin-4-amine.

STIMULATION OF $^3$H-THYMIDINE UPTAKE IN CULTURES OF HUMAN PERIPHERAL BLOOD MONONUCLEAR CELLS

The test method described below demonstrates the ability of compounds to stimulate the uptake of $^3$H-thymidine in human cells. Increased uptake of $^3$H-thymidine indicates that the cells are actively dividing.

Blood Cell Preparation for Culture

Whole blood is collected by venipuncture into heparin vacutainer tubes. Peripheral blood mononuclear cells (PBMC) are isolated using Ficoll-Paque® solution (available from Pharmacia LKB Biotechnology Inc., Piscataway, N.J.). The PBMC are washed with Hank's Balanced Salts Solution then diluted with RPMI 1640 medium containing 2.0 Mm L-glutamine, 10% fetal calf serum and 1% penicillin/streptomycin to obtain a concentration of 2×10$^6$ cells/mL.

Compound Preparation

The compounds are dissolved in water then diluted with the medium used above to give the desired concentration.

Incubation

A 0.1 mL portion of compound solution is added to the wells (3 wells for each treatment) of a 96 well round bottom tissue culture plate. Control wells receive 0.1 mL portions of medium. A 0.1 mL portion of cell suspension (1×10$^5$ cells) is added to each well and the plates are incubated for 48 hours at 37° C. in the presence of 5% carbon dioxide. During the last 4 to 6 hour of culture 1 µCi of $^3$H-thymidine (having a specific activity of 6.7 Ci/mmole; available from New England Nuclear) is added to each well.

$^3$H-Thymidine Uptake Measurement/Analysis

Cultures are harvested and collected on glass fiber filter strips. Each strip is placed in a scintillation vial. A 1 to 2 mL portion of Aquasol®-2 Universal LSC Cocktail (available from DuPont) is added to each well. After 15 minutes the radioactivity is counted for 1 minute in a scintillation counter. A stimulation index (SI) is calculated by dividing the counts per minute from the treatment wells by the counts per minute from the control wells.

Results are shown in the table below. Concentrations are the final concentrations found in the well after the addition of the cell suspension. The CPM value is the mean CPM of the three wells for each treatment. Phytohemagglutinin (PHA) and lipopolysaccharide (LPS) are included as reference agents.

| STIMULATION OF $^3$H-THYMIDINE UPTAKE IN CULTURES OF HUMAN PERIPHERAL BLOOD MONONUCLEAR CELLS | | |
|---|---|---|
| TREATMENT | CPM ± SEM | SI |
| Medium | 4,859 ± 392 | 1.0 |
| PHA (5 µg/mL) | 59,818 ± 2,867 | 12.3 |
| LPS (2 µg/mL) | 3,228 ± 433 | 0.7 |
| Compound C (4 µg/mL) | 30,119 ± 636 | 6.2 |
| Compound C (1 µg/mL) | 29,596 ± 3,221 | 6.1 |
| Compound C (0.25 µg/mL) | 43,055 ± 9,383 | 8.9 |
| Compound C (0.06 µg/mL) | 24,336 ± 2,756 | 5.0 |

STIMULATION OF $^3$H-THYMIDINE UPTAKE BY MURINE SPLEEN CELLS

The test method described below demonstrates the ability of compounds to stimulate the uptake of $^3$H-thymidine by murine spleen cells. Increased uptake of $^3$H-thymidine indicates that the cells are actively dividing.

Spleen Cell Preparation for Culture

Spleens are aseptically removed from male CFW mice 4 to 8 weeks of age and placed in 10 mL of Hank's Balanced Salts Solution (HBSS). A scalpel is used to remove the cells from the capsule. A single cell suspension is prepared by pipetting the suspension several times using a 5.0 mL syringe equipped with a 19 gauge needle. The suspension is transferred to a 15 mL centrifuge tube and allowed to stand on ice for 4 minutes. The supernatant is removed with a 10 mL pipet, transferred to a clean 15 mL centrifuge tube and centrifuged at 1200 rpm for 5 to 10 minutes. The supernatant is discarded. To remove the red blood cells, the pellet is resuspended in 5 mL of 0.15M ammonium chloride, let stand at room temperature for 5 minutes and then centrifuged at 1200 rpm for 5 to 10 minutes. The supernatant is discarded. The pellet is twice resuspended in 10 mL HBSS then centrifuged at 1200 rpm for 5 to 10 minutes. The supernatant is discarded. The pellet is resuspended in RPMI 1640 medium containing 2.0 mM L-glutamine, 10% fetal calf serum, 1% penicillin/streptomycin and 5×10$^{-5}$M 2-mercaptoethanol. The cells are counted then diluted with medium to give a concentration of 2×10$^6$ cells/mL.

Compound Preparation

The compounds are dissolved in water then diluted with medium to give the desired concentration.

Incubation

The same procedures and conditions as described above for uptake in PBMC are used.

$^3$H-Thymidine Uptake Measurement/Analysis

The same procedures and methods as described above for uptake in PBMC are used.

Results are shown in the table below. Concentrations are the final concentrations found in the well after the addition of the cell suspension. The CPM value is the mean CPM of the three wells for each treatment. Concanavalin A (ConA), lipopolysaccharide (LPS), staphylococcal enterotoxin B (SEB) and polyriboinosinic acid-polyribocytidylic acid (Poly IC) are included as reference agents.

| STIMULATION OF $^3$H-THYMIDINE UPTAKE BY MURINE SPLEEN CELLS | | |
|---|---|---|
| TREATMENT | CPM | SI |
| Medium | 13,728 | 1.0 |
| ConA (5 µg/mL) | 488,180 | 35.6 |
| LPS (5 µg/mL) | 114,023 | 8.3 |
| SEB (1 µg/mL) | 303,213 | 24.2 |
| Poly IC (5 µg/mL) | 36,102 | 2.6 |
| Compound | | |
| C     (1 µg/mL) | 161,573 | 11.8 |
| C     (0.1 µg/mL) | 147,356 | 10.7 |
| C     (0.01 µg/mL) | 67,960 | 5.0 |
| C     (0.001 µg/mL) | 20,004 | 1.4 |
| C     (0.0001 µg/mL) | 17,759 | 1.3 |
| A     (1 µg/mL) | 149,940 | 10.9 |
| A     (0.1 µg/mL) | 87,753 | 6.4 |
| A     (0.01 µg/mL) | 21,188 | 1.5 |
| A     (0.001 µg/mL) | 21,270 | 1.5 |
| B     (1 µg/mL) | 146,980 | 10.7 |
| B     (0.1 µg/mL) | 51,880 | 3.8 |
| B     (0.01 µg/mL) | 19,525 | 1.4 |
| B     (0.001 µg/mL) | 20,596 | 1.5 |
| B     (0.0001 µg/mL) | 22,076 | 1.6 |
| D     (1 µg/mL) | 174,203 | 12.7 |
| D     (0.1 µg/mL) | 165,630 | 12.1 |
| D     (0.01 µg/mL) | 180,606 | 13.2 |
| D     (0.001 µg/mL) | 116,380 | 8.5 |
| D     (0.0001 µg/mL) | 25,689 | 1.9 |

STIMULATION OF ANTIBODY PRODUCTION IN MURINE SPLEEN CELLS

The test method described below demonstrates the ability of compounds to stimulate antibody production in murine spleen cells.

Spleen Cell Preparation for Culture

The spleen cells are prepared as described above except that they are diluted in 6 well tissue culture plates to give a final concentration of 1×10$^7$ cells/mL.

Compound Preparation

The compounds are dissolved in water then diluted with medium to give the desired concentration.

Incubation

A 0.1 mL portion of compound solution is added to each well (2 wells for each treatment). Control wells receive medium. The final volume in the well is adjusted to 1 mL with medium. The plates are incubated for 72 hours at 37° C. in the presence of 5% carbon dioxide.

Antibody Production Measurement/Analysis

Antibody production is measured by utilizing a modified Jerne Plaque Assay. Briefly stated, the method is as follows. Plastic culture dishes are coated with 2 mL of poly-L-lysine (50 µg/mL). After 15 minutes the plates are washed with phosphate buffered saline (PBS) and 2 mL of washed sheep red blood cells (SRBC) diluted 1:20 in PBS is added. After 15 minutes the plates are swirled, allowed to settle for another 15 minutes and rinsed with buffered saline. Finally, 1.5 mL of phosphate-buffered saline, pH 7.2, is added to each plate along with 2.5×10$^5$ spleen cells. The plates are then incubated in the presence of guinea pig complement at 37° C. for 1 hour, after which plaque forming cells (PFC) are counted under slight magnification. Results are presented as the mean PFC/culture±SEM (standard error of the mean). A stimulation index (SI) is calculated by dividing the PFC from the treatment wells by the PFC from the control (medium) wells.

Results are shown in the table below. Concentrations are the final concentrations found in the well after both the cell suspension and the compound solution have been added. The PFC value is the mean PFC of the 2 wells for each treatment group. Lipopolysaccharide (LPS) and polyriboinosinic acid-polyribocytidylic acid (PIC) are included as reference agents.

| STIMULATION OF ANTIBODY PRODUCTION IN MURINE SPLEEN CELLS | | | |
|---|---|---|---|
| TREATMENT | PFC/Culture | SI | PFC/10$^6$ cells |
| Medium | 167 ± 18 | 1.0 | 30 |
| LPS (10 µg/mL) | 1,555 ± 208 | 9.3 | 179 |
| LPS (3 µg/mL) | 1,300 ± 391 | 7.8 | 118 |
| LPS (1 µg/mL) | 1,150 ± 232 | 6.9 | 153 |
| PIC (10 µg/mL) | 604 ± 227 | 3.6 | 106 |
| PIC (3 µg/mL) | 365 ± 142 | 2.2 | 49 |
| PIC (1 µg/mL) | 273 ± 15 | 1.6 | 29 |
| Compound | | | |
| C   (10 µg/mL) | 1,419 ± 219 | 8.5 | 121 |
| C   (3 µg/mL) | 1,271 ± 67 | 7.6 | 190 |
| C   (1 µg/mL) | 1,465 ± 311 | 8.8 | 274 |

STIMULATION OF B CELLS IN MURINE SPLEEN CELLS

The test method described below demonstrates the ability of compounds to stimulate B cells in murine spleen cells.

Spleen Cell Preparation for Culture

Spleen cells are prepared as described above in connection with the uptake of $^3$H-thymidine.

Compound Preparation

The compounds are dissolved in water then diluted with medium to give the desired concentration.

Incubation

A 0.9 mL portion of cell suspension is added to each well of a 12 well tissue culture plate. A 0.1 mL portion of compound solution is added to the wells (2 wells for each treatment). Control wells receive 0.1 mL portions of medium. The plates are incubated for 72 hours at 37° C. in the presence of 5% carbon dioxide.

Quantitation of B and T Cells

The cell culture is removed from the well, combined with the culture from the second well, and washed twice with Hanks Balanced Salts Solution. The cells are diluted with phosphate buffered saline (PBS) supplemented with 1% fetal calf serum (FCS) to give a concentration of 1×10$^6$ cells/100 µL. The cells are stained with antibody for 30 minutes at 4° C. Fluorescein isothiocyanate labeled goat anti-mouse immunoglobulin antibody (FITC αI$_G$) functions as the B cell marker. Fluorescein isothiocyanate labeled anti mouse Thy 1.2 antibody functions as the T cell marker. The cells are then washed twice with PBS supplemented with 1% FCS then analyzed for fluorescence using a Becton Dickinson FACSCAN. The results are reported as the percentage of the total cells, both the whole (unseparated) cells and the blast-like cells, that are positive for the marker.

The results are shown in the table below. The concentrations are the final concentrations in the well after both the cell suspension and the compound solution have been added. Lipopolysaccharide is included as a reference agent.

| QUANTITATION OF B AND T CELLS IN MURINE SPLEEN CELL CULTURES | | | | |
|---|---|---|---|---|
| | FITC α $I_G$ | | FITC Anti Thy 1.2 | |
| TREATMENT | Whole | Blast | Whole | Blast |
| Medium | 56.5 | — | 34.7 | — |
| LPS (5 µg/mL) | 73.1 | 93.6 | 15.5 | 9.4 |
| Compound | | | | |
| C (4 µg/mL) | 72.3 | 97.1 | 14.1 | 10.7 |
| C (1 µg/mL) | 75.0 | 97.0 | 14.1 | 7.3 |
| C (0.25 µg/mL) | 74.0 | 96.0 | 12.8 | 9.9 |

ENHANCEMENT OF ANTIBODY FORMATION IN MICE

The test method described below demonstrates the ability of compounds to enhance antibody formation in mice to sheep red blood cells (a T-dependent antigen).

On day 0, male CFW mice 4 to 8 weeks of age are injected intraperitoneally with sheep red blood cells ($1 \times 10^7$ in phosphate buffered saline). Also on day 0, test compounds are dissolved in sterile water then injected intraperitoneally (3 mice for each treatment). On day 4 the mice are sacrificed and the spleens are removed. Single cell suspensions are prepared in phosphate buffered saline to give a final concentration of $5 \times 10^5$ cells/mL for use in a modified Jerne Plaque Assay. The assay is performed as described above in connection with antibody formation in spleen cell cultures. The results are reported as plaque forming cells (PFC) per $10^6$ cells and per spleen. A stimulation index (SI) is calculated by dividing the PFC value for the treatment group by the PFC value for the control (SRBC but no compound) group.

Results are shown in the table below. Values are the average number of plaque forming cells (PFC)±SEM. Each data point is the average of three mice pooled. Lipopolysaccharide (LPS) and polyriboinosinic acid-polyribocytidylic acid (Poly IC) are included as reference agents.

| ENHANCEMENT OF ANTIBODY PRODUCTION IN MICE | | | |
|---|---|---|---|
| TREATMENT | PFC/ $10^6$ CELLS | PFC/ SPLEEN | SI |
| Saline | 1 | 11 | |
| SRBC | 7 ± 1 | 473 | 1.0 |
| LPS (1 mg/Kg) + SRBC | 246 ± 24 | 12,054 | 35.1 |
| Poly IC (100 µg/Kg) + SRBC | 74 ± 11 | 5,180 | 10.5 |
| Compound C (10 mg/Kg) + SRBC | 21 ± 2 | 1,372 | 3.0 |
| Compound C (3 mg/Kg) + SRBC | 82 ± 7 | 6,123 | 11.7 |
| Compound C (1 mg/Kg) + SRBC | 58 ± 7 | 3,789 | 8.3 |

SUPPRESSION OF ANTIBODY FORMATION IN MICE

This test method is the same as the one described above for enhancement of antibody formation except that the compounds are administered on day minus 1 and $1 \times 10^8$ SRBC are administered on day 0. The percent suppression is calculated as follows:

$$\frac{(PFC \text{ value of } SRBC \text{ only} - PFC \text{ value of treatment})}{PFC \text{ value of } SRBC \text{ only}} \times 100$$

The results are shown in the table below.

| SUPPRESSION OF ANTIBODY FORMATION IN MICE | | | |
|---|---|---|---|
| TREATMENT | PFC/ $10^6$ CELLS | PFC/ SPLEEN | % SUPPRESS |
| Saline | 1 ± 1 | 38 | — |
| SRBC | 594 ± 41 | 34,000 | — |
| Compound C (1 mg/Kg) + SRBC | 129 ± 16 | 9,500 | 78.3 |
| Compound C (3 mg/Kg) + SRBC | 87 ± 8 | 6,700 | 85.4 |
| Compound C (1 mg/Kg) + saline day 0 | 3 ± 1 | 220 | — |

The experiments set forth below illustrate the adjuvant effect in guinea pigs of 1-(2-methylpropyl)-1H-imidazo[4,5-c]quinolin-4-amine used in connection with a herpes simplex 2 (HSV-2) glycoprotein subunit vaccine.

HSV-2 Glycoprotein Preparation

HSV-2 (strain MS) infected Vero cells were solubilized and the glycoproteins were purified by lentil-lectin sepharose chromatography. The final preparation contained all three HSV-2 glycoproteins, gB, gD, and gG, that were evaluated. The glycoprotein preparation was diluted to contain 35 µg/0.1 mL total glycoprotein. Glycoprotein administration is described below in connection with the experimental design.

Treatment Groups 1-(2-methylpropyl)-1H-imidazo[4,5-c]quinolin-4-amine (one percent by weight in a cream containing water (76.5%), isosteric acid (10%), stearyl alcohol (3.1%), polysorbate 60 (2.55%), cetyl alcohol (2.2%), benzyl alcohol (2%), glycerin (2%), sorbitan monostearate (0.45%), methylparaben (0.2%), and propylparaben (0.02%) was administered to guinea pigs as described below intravaginally at a concentration of 5 mg/kg/day for 5 days beginning either simultaneously with glycoprotein administration ("S group"), or after a delay of 48h after glycoprotein administration ("D group"). The hydrochloride salt was administered in water subcutaneously at a dose of 3 mg/kg/day for 5 days beginning simultaneously with glycoprotein administration ("subQ S group"). Complete Freund's adjuvant ("CFA", Sigma) was administered as a 1:1 mixture of the adjuvant and the glycoprotein ("CFA Group"). An unimmunized infected control group was maintained. Also one group was given the glycoprotein alone ("glycoprotein group").

Experimental Design

Hartley female guinea pigs (Charles River Breeding Laboratory, Wilmington, Mass.) weighing 200–300 g were immunized with 35 µg of HSV-2 glycoproteins in the hind footpads, first 35 days prior to vaginal inoculation with HSV-2 and again 14 days prior to inoculation.

Animals were inoculated intravaginally with $10^{5.7}$ pfu of either 333 strain HSV-2 (first experiment) or MS strain (ATCC VR-540) HSV-2 (second experiment). Samples of vaginal secretions were then collected over the next 10 days and stored frozen at −70° C. prior to assay on Vero cells for viral concentration. During the acute infection period (days 1–14), animals were evaluated daily for genital skin disease which was quantitated on a scale of 0–4 as described in *J. Infect. Dis.*, 1982, 146, 397 (Stanberry et al.). Total lesion scores are the sum of these scores for days 1 through 14. After recovery from the acute infection, animals were examined daily from day 15–60 for evidence of recurrent herpetic disease. Sera were collected from immunized animals just prior to intravaginal inoculation and again 14, 44, or 60 days later.

Enzyme-linked Immunosorbent Assay for HSV-2 Antibodies

HSV-2 antibodies were quantified by an ELISA assay. Lectin purified HSV-2 glycoproteins were used as the solid phase and peroxidase-conjugated rabbit anti-guinea pig immunoglobulins (Accurate Chemical, Westbury, N.Y.) were used for detection of guinea pig antibody. Absorbances were compared to a standardized control serum arbitrarily assigned a value of 10,000 ELISA units.

Statistics

Comparison of lesion scores for acute disease, viral shedding, and recurrent lesion days were done by two-tailed ANOVA with the Bonferroni correction to adjust for multiple groups. Data are expressed as mean±S.E.

Acute Disease

To determine if 1-(2-methylpropyl)-1H-imidazo[4,5-c]quinolin-4-amine would increase the effectiveness of an HSV-2 glycoprotein vaccine, five treatment groups of 11 guinea pigs were used as follows:

1) unimmunized control group;
2) glycoprotein group;
3) D Group;
4) S Group; and
5) CFA Group.

Immunization with the HSV-2 glycoproteins alone significantly reduced the total lesion score from 19.1±3.2 in the unimmunized control group to 3.9±0.9 ($p<0.001$). Because of the mild disease in the glycoprotein group, no further significant reduction could be demonstrated for the other groups, although the total lesion score was less for each of the groups receiving a vaccine adjuvant treatment. (D group, 2.8±0.7; S Group, 2.2±0.6; CFA Group, 1.2±0.5).

Immunization with glycoprotein alone and also with the several adjuvant preparations reduced vaginal viral shedding compared to the unimmunized infected control group.

Recurrent Disease

The recurrence pattern was similar for the unimmunized control group and glycoprotein group (4.9±0.9 vs. 4.3±0.9 recurrent lesion days, respectively). The use of 1-(2-methylpropyl)-1H-imidazo[4,5-c]quinolin-4-amine as an adjuvant, however, significantly reduced recurrent lesion days to 0.8±0.3 and 0.1±0.1, respectively, for the S Group and D Group ($p<0.01$ for each compared to the glycoprotein group). only one of ten animals in the S Group developed a recurrence, while eight of nine recipients of glycoprotein alone ($p<0.002$) developed a recurrence. Three of ten animals in the CFA Group developed recurrent lesions.

Antibody Response

Compared to the glycoprotein group, antibody titers on the day of inoculation were marginally increased in the S Group ($p<0.05$), but increased by over tenfold in the CFA Group ($p<0.001$). Peak antibody titers (day 44) in the unimmunized infected control group approached the level induced in the glycoprotein group. The CFA Group titers were higher than the unimmunized control group and the groups receiving 1-(2-methylpropyl)-1H-imidazo[4,5-c]quinolin-4-amine as a vaccine adjuvant.

The experiment described above was repeated, with the addition of two treatment groups, in order to examine the effects of 1-(2-methylpropyl)-1H-imidazo[4,5-c]quinolin-4-amine given subcutaneously with glycoprotein ("SubQ S Group"), and the effects of 1-(2-methylpropyl)-1H-imidazo[4,5-c]quinolin-4-amine alone ("Compound Group").

A pool of HSV-2 MS strain that had previously produced milder acute disease but more frequent recurrences was used in order to better observe effects on recurrent disease.

Acute Disease

The only groups to develop lesions acutely were the unimmunized groups (Compound Group, 9 of 9; unimmunized control group, 11 of 11) and the glycoprotein group (6 of 11). Again, because of the significant effect of immunization with glycoprotein alone, only small adjuvant effects of 1-(2-methylpropyl)-1H-imidazo[4,5-c]quinolin-4-amine on the severity of the acute disease could be demonstrated (differences in total lesion score ($p<0.05$) for each compared to glycoprotein alone).

Vaginal viral shedding was also decreased by immunization with glycoprotein alone. The use of 1-(2-methylpropyl)-1H-imidazo[4,5-c]quinolin-4-amine as an adjuvant, however, further decreased viral shedding. Compared to glycoprotein alone, viral shedding was decreased tenfold in the D Group, by another tenfold in the S Group ($p<0.05$), and by yet another tenfold in the SubQ S Group ($p<0.001$) on day one. Thus, there was >99.9% reduction in the SubQ S Group compared to the glycoprotein group and a >99.9% reduction compared to the unimmunized control group. No virus was detected in the CFA group. Treatment with 1-(2-methylpropyl)-1H-imidazo[4,5-c]quinolin-4-amine alone had no significant effect on vaginal viral shedding.

Recurrent Disease

Results are shown in the Table below:

| EFFECT OF ADJUVANT ON THE PATTERN OF RECURRENT GENITAL HSV-2 DISEASE | | |
|---|---|---|
| Group | Animals with recurrent lesions | No. days with herpetic lesions[a] |
| Unimmunized control | 11/11 | 5.7 ± 0.8 |
| Glycoprotein | 9/11 | 2.5 ± 0.9[e] |
| D Group | 4/11 | 0.4 ± 0.2[b] |
| S Group | 3/11[b] | 0.3 ± 0.1[b] |
| SubQ S Group | 0/11[c] | 0[d] |
| CFA Group | 0/11[c] | 0[d] |
| Compound Group | 8/11 | 1.8 ± 0.5 |

[a] Mean ± SE per animal of days with recurrent herpetic lesions
[b] $P < .05$ compared to Glycoprotein group
[c] $P < .001$ compared to Glycoprotein group
[d] $P < .01$ compared to Glycoprotein group
[e] $P < .001$ compared to unimmunized control Immunization with the glycoproteins alone significantly reduced recurrent lesion days compared to unimmunized controls ($p<0.01$), but not the number of animals with recurrences. Compared to the glycoprotein alone, however, the use of 1-(2-methylpropyl)-1H-imidazo[4,5-c]quinolin-4-amine as an adjuvant further significantly reduced recurrent lesion days and reduced the number of animals with recurrences. None of the animals in the SubQ S Group developed recurrences ($p<0.001$ compared to glycoprotein alone). The Compound Group also developed significantly fewer recurrences than the unimmunized control group ($p<0.001$).

Antibody Response

Antibody titers in the CFA group were again over tenfold higher than the glycoprotein group ($p<0.001$) and the D Group, S Group, and SubQ S Group ($p<0.01$). Groups that received 1-(2-methylpropyl)-1H-imidazo[4,5-c]quinolin-4-amine as an adjuvant did not, however, develop higher titers of HSV-2 antibody than the glycoprotein group. The Compound Group developed higher antibody titers than the unimmunized control group ($p<0.05$).

The results above indicate that 1-(2-methylpropyl)-1H-imidazo[4,5-c]quinolin-4-amine augments the ability of the HSV-2 glycoprotein vaccine to decrease viral replication at the mucosal site, prevent clinical disease, and decrease the number of recurrences that develop after infection.

The most effective regimen involved subcutaneous administration for 5 doses beginning at the time of immunization. The results were comparable to using CFA as an adjuvant. Animals that received intravaginal administration had decreased viral titers and fewer recurrent lesion days.

The addition of 1-(2-methylpropyl)-1H-imidazo[4,5-c]quinolin-4-amine to glycoprotein immunization had little effect on antibody titers but significantly increased the protection provided by the glycoprotein preparation especially against recurrent disease.

We claim:

1. A vaccine adjuvant composition comprising a vaccine in an amount effective to stimulate a cell-mediated immune response and as a vaccine adjuvant a 1H-imidazo[4,5-c]quinolin-4-amine or derivatives thereof, in an amount effective to potentiate the cell-mediated immune response to the vaccine.

2. An immunogen/vaccine adjuvant composition according to claim 1, wherein the 1H-imidazo[4,5-c]quinolin-4-amine is a compound defined by one of Formulas I–V:

I 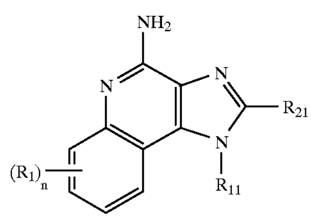 wherein $R_{11}$ is selected from the group consisting of alkyl, hydroxyalkyl, acyloxyalkyl, benzyl, (phenyl)ethyl and phenyl, said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that if said benzene ring is substituted by two of said moieties, then said moieties together contain no more than 6 carbon atoms; $R_{21}$ is selected from the group consisting of hydrogen, alkyl of one to about eight carbon atoms, benzyl, (phenyl)ethyl, and phenyl, the benzyl (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when the benzene ring is substituted by two of said moieties, then the moieties together contain no more than 6 carbon atoms; and each $R_1$ is independently selected from the group consisting of alkoxy of one to about four carbon atoms, halogen, and alkyl of one to about four carbon atoms, and n is an integer from 0 to 2, with the proviso that if n is 2, then said $R_1$ groups together contain no more than 6 carbon atoms;

II 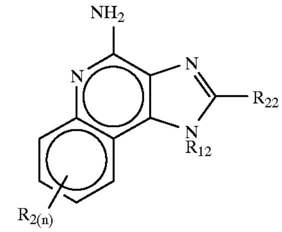 wherein $R_{12}$ is selected from the group consisting of straight chain or branched chain alkenyl containing 2 to about 10 carbon atoms and substituted straight chain or branched chain alkenyl containing 2 to about 10 carbon atoms, wherein the substituent is selected from the group consisting of straight chain or branched chain alkyl containing 1 to about 4 carbon atoms and cycloalkyl containing 3 to about 6 carbon atoms; and cycloalkyl containing 3 to about 6 carbon atoms substituted by straight chain or branched chain alkyl containing 1 about 4 carbon atoms; and $R_{22}$ is selected from the group consisting of hydrogen, straight chain or branched chain alkyl containing one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to about four carbon atoms, straight chain or branched chain alkoxy containing one to about four carbon atoms, and halogen, with the proviso that when the benzene ring is substituted by two such moieties, then the moieties together contain no more than 6 carbon atoms; and each $R_2$ is independently selected from the group consisting of straight chain or branched chain alkoxy containing one to about four carbon atoms, halogen, and straight chain or branched chain alkyl containing one to about four carbon atoms, and n is an integer from zero to 2, with the proviso that if n is 2, then said $R_2$ groups together contain no more than 6 carbon atoms;

III 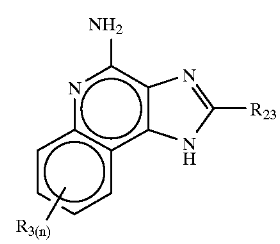 wherein $R_{23}$ is selected from the group consisting of hydrogen, straight chain or branched chain alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl of one to about four carbon atoms, straight chain or branched chain alkoxy of one to about four carbon atoms, and halogen, with the proviso that when the benzene ring is substituted by two such moieties, then the moieties together contain no more than 6 carbon atoms; and each $R_3$ is independently selected from the group consisting of straight chain or branched chain alkoxy of one to about four carbon atoms, halogen, and straight chain or branched chain alkyl of one to about four carbon atoms, and n is an integer from zero to 2, with the proviso that if n is 2, then said R groups together contain no more than 6 carbon atoms;

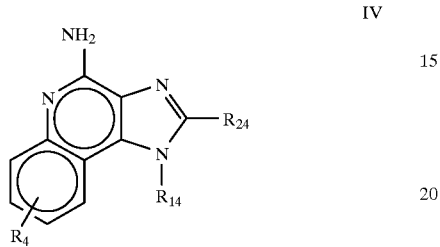

IV wherein $R_{14}$ is —CHR$_A$R$_B$ wherein $R_B$ is hydrogen or a carbon-carbon bond, with the proviso that when $R_B$ is hydrogen $R_A$ is alkoxy of one to about four carbon atoms, hydroxyalkoxy of one to about four carbon atoms, 1-alkynyl of two to about ten carbon atoms, tetrahydropyranyl, alkoxyalkyl wherein the alkoxy moiety contains one to about four carbon atoms and the alkyl moiety contains one to about four carbon atoms, 2-, 3-, or 4-pyridyl, and with the further proviso that when $R_B$ is a carbon-carbon bond $R_B$ and $R_A$ together form a tetrahydrofuranyl group optionally substituted with one or more substituents independently selected from the group consisting of hydroxy and hydroxyalkyl of one to about four carbon atoms;

$R_{24}$ is selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and $R_4$ is selected from the group consisting of hydrogen, straight chain or branched chain alkoxy containing one to about four carbon atoms, halogen, and straight chain or branched chain alkyl containing one to about four carbon atoms;

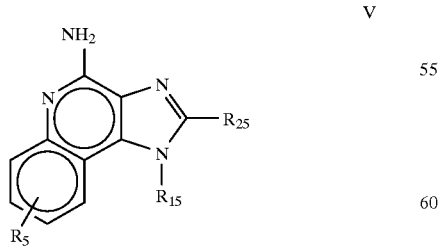

V wherein $R_{15}$ is selected from the group consisting of: hydrogen; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;

$R_{25}$ is

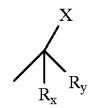

wherein $R_x$ and $R_y$ are independently selected from the group consisting of hydrogen, alkyl of one to about four carbon atoms, phenyl, and substituted phenyl wherein the substituent is elected from the group consisting of alkyl of one to about four carbon atoms, alkoxy of one to about four carbon atoms, and halogen;

X is selected from the group consisting of alkoxy containing one to about four carbon atoms, alkoxyalkyl wherein the alkoxy moiety contains one to about four carbon atoms and the alkyl moiety contains one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, alkylthio of one to about four carbon atoms; and $R_5$ is selected from the group consisting of hydrogen, straight chain or branched chain alkoxy containing one to about four carbon atoms, halogen, and straight chain or branched chain alkyl containing one to about four carbon atoms;

or a pharmaceutically acceptable salt thereof.

3. A composition according to claim 1, wherein the 1H-imidazo[4,5-c] quinolin-4-amine is a compound of Formula VI:

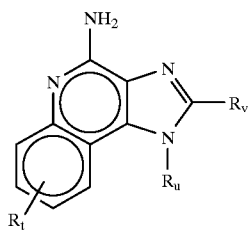

wherein
- $R_t$ is selected from the group consisting of hydrogen, straight chain or branched chain alkoxy containing one to about four carbon atoms, halogen, and straight chain or branched chain alkyl containing one to about four carbon atoms;
- $R_u$ is 2-methylpropyl or 2-hydroxy-2-methylpropyl; and
- $R_v$ is hydrogen, alkyl of one to about six carbon atoms, or alkoxyalkyl wherein the alkoxy moiety contains one to about four carbon atoms and the alkyl moiety contains one to about four carbon atoms.

4. A composition according to claim 3, wherein $R_t$ is hydrogen.

5. A composition according to claim 3, wherein $R_t$ is hydrogen, $R_u$ is 2-methylpropyl or 2-hydroxy-2-methylpropyl, and $R_v$ is hydrogen, methyl, or ethoxymethyl.

6. A composition according to claim 1, wherein the derivative thereof are selected from the group consisting of 1-(2-methylpropyl)-1H-imidazo[4,5-c]quinolin-4-amine; 1-(2-hydroxy-2-methylpropyl)-1H-imidazo[4,5-c]quinolin-4-amine; 1-(2-hydroxy-2-methylpropyl)-2-methyl-1H-imidazo[4,5-c]quinolin-4-amine; and 1-(2-hydroxy-2-methylpropyl)-2-ethoxymethyl-1H-imidazo[4,5-c]quinolin-4-amine.

7. A composition according to claim 1, wherein the vaccine is selected from the group consisting of a live viral vaccine, a live bacterial vaccine, an inactivated viral vaccine, an inactivated tumor-derived vaccine, an inactivated protozoal vaccine, an inactivated organism-derived vaccine, an inactivated fungal vaccine, an inactivated bacterial vaccine, a toxoid, a toxin, a polysaccharide, a protein, a glycoprotein, and a peptide.

8. A composition according to claim 1, wherein the vaccine is a conventional vaccine preparation.

9. A composition according to claim 1, wherein the vaccine is a recombinant subunit vaccine.

10. A composition according to claim 1, wherein the vaccine is a T-dependent vaccine.

11. A composition according to claim 1, wherein the vaccine is herpes simplex 2 glycoprotein subunit preparation.

12. A composition according to claim 1, comprising an admixture of the 1H-imidazo[4,5-c]quinolin-4-amine and the vaccine in a pharmaceutically acceptable carrier.

13. A composition according to claim 1 in the form of a kit comprising (i) an adjuvant component comprising the 1H-imidazo[4,5-c]quinolin-4-amine, and (ii) a vaccine component separate from the adjuvant component.

14. A method of increasing the immune response to a vaccine, comprising the step of administering (i) the vaccine in an amount effective to stimulate a cell-mediated immune response, and (ii) as a vaccine adjuvant a 1H-imidazo[4,5-c]quinolin-4-amine in an amount effective to potentiate the cell-mediated immune response to the vaccine.

15. A method of increasing the immune response of a mammal to a vaccine, comprising the step of administering to the mammal (i) the vaccine in an amount effective to stimulate a cell-mediated immune response, and (ii) as a vaccine adjuvant a 1H-imidazo[4,5-c]quinolin-4-amine in an amount effective to potentiate the cell-mediated immune response to the vaccine.

16. A method of increasing the immune response of a fowl to a vaccine, comprising the step of administering to the fowl (i) the vaccine in an amount effective to stimulate a cell-mediated immune response, and (ii) as a vaccine adjuvant a 1H-imidazo[4,5-c]quinolin-4-amine in an amount effective to potentiate the cell-mediated immune response to the vaccine.

* * * * *

UNITED STATES PATENT AND TRADEMARK OFFICE
CERTIFICATE OF CORRECTION

PATENT NO. : 6,083,505
DATED : July 4, 2000
INVENTOR(S) : Richard L. Miller, Mark A. Tomai, David I. Bernstein, and Christopher J. Harrison It is certified that error appears in the above-identified patent and that said Letters Patent is hereby corrected as shown below:

Column 5,
Lines 25 through 34, please delete structure.

Column 6,
Lines 12 through 21, please delete structure.

Signed and Sealed this

Nineteenth Day of March, 2002

Attest:

JAMES E. ROGAN
Director of the United States Patent and Trademark Office

Attesting Officer